US008506507B2

(12) United States Patent
Bock

(10) Patent No.: US 8,506,507 B2
(45) Date of Patent: Aug. 13, 2013

(54) VENOUS AUGMENTATION SYSTEM

(75) Inventor: Malcolm G. Bock, Medfield, MA (US)

(73) Assignee: Covidien LP, Mansfield, MA (US)

( * ) Notice: Subject to any disclaimer, the term of this patent is extended or adjusted under 35 U.S.C. 154(b) by 575 days.

(21) Appl. No.: 12/720,122

(22) Filed: Mar. 9, 2010

(65) Prior Publication Data

US 2011/0224589 A1 Sep. 15, 2011

(51) Int. Cl.

*A61H 7/00* (2006.01)
*A61H 19/00* (2006.01)
*A61B 17/00* (2006.01)

(52) U.S. Cl.

USPC ............................ 601/150; 601/152; 606/202

(58) Field of Classification Search

USPC ........... 601/148-153; 602/13; 606/201-204; 128/DIG. 20

See application file for complete search history.

(56) References Cited

U.S. PATENT DOCUMENTS 3,811,431 A 5/1974 Apstein
3,866,604 A 2/1975 Curless et al.
3,942,518 A 3/1976 Tenteris et al.
3,961,625 A 6/1976 Dillon
4,186,732 A 2/1980 Christoffel
4,419,988 A 12/1983 Mummert
5,050,613 A 9/1991 Newman et al.
5,307,791 A 5/1994 Senoue et al.
5,396,896 A 3/1995 Tumey et al.
5,968,073 A 10/1999 Jacobs
6,231,532 B1 5/2001 Watson et al.
6,858,012 B2 2/2005 Burns et al.
7,618,384 B2 11/2009 Nardi et al.
2001/0000262 A1 4/2001 McEwen et al.
2005/0187500 A1 8/2005 Perry et al.
2006/0149176 A1 7/2006 Bolam et al.

FOREIGN PATENT DOCUMENTS

DE 42 18 340 A1 12/1992

OTHER PUBLICATIONS

PCT International Search Report for PCT/US2011/027163 with Written Opinion of the International Searching Authority dated Aug. 11, 2011, 14 pages.

*Primary Examiner* — Nicholas Lucchesi
*Assistant Examiner* — Nathan R Price
(74) *Attorney, Agent, or Firm* — John Paul Mello, Esq.

(57) ABSTRACT

A method for augmenting blood flow in a limb that is wrapped with a sleeve having at least one chamber for applying compression to the limb in a region generally underlying the chamber includes pressurizing the chamber to a first compression pressure and then reducing the pressure to a refill pressure. Pressure in the chamber is then sensed to determine a first venous refill time. The preceding steps are repeated a second and other times using second and other compression pressures that are different from the first compression pressure and from each other to determine second and other venous refill times. A customized compression pressure is determined by locating the compression pressure at which blood flow out of the region generally underlying the chamber is maximized by finding compression pressure at a maximum venous refill time. A compression device employing such a method is also disclosed.

7 Claims, 6 Drawing Sheets

VENOUS AUGMENTATION SYSTEM

FIELD OF THE INVENTION

The present invention generally relates to compression sleeves, and more particularly, compression sleeves for optimizing vascular refill.

BACKGROUND OF THE INVENTION

The pooling of blood or stasis in a patient's extremities, particularly the legs, occurs when the patient is confined to bed for an extended period of time. Stasis is problematic because it is a significant cause leading to the formation of thrombi. To prevent this occurrence, it is desirable to move fluid out of interstitial spaces in the extremity tissues to enhance circulation.

Intermittent pneumatic compression (IPC) devices are used to improve circulation and minimize the formation of thrombi in the limbs of patients. An example of one such IPC device is disclosed in U.S. Pat. No. 6,231,53. These devices typically include a compression sleeve or garment having one or more inflatable chambers configured to provide a compressive pulse to the limb. The chamber or chambers are maintained in the inflated state for a predetermined period of time and then deflated. After another predetermined time the chamber or chambers are re-inflated. This vascular refill process increases blood circulation and minimizes the formation of thrombi. During this process the pressure in the chamber or chambers can be monitored to adjust the vascular refill time in response to changing conditions of the patient.

Currently IPC devices are operated using a single predetermined chamber inflation pressure. However, due to the variability in patient's extremities, these devices have inherent shortcomings. Accordingly, there is a need for an IPC device capable of obtaining a more optimum vascular refill for a variety of limb shapes and sizes.

SUMMARY OF THE INVENTION

In one aspect, a method for augmenting blood flow in a limb that is wrapped with a sleeve having at least one chamber capable of being pressurized for applying compression to the limb in a region generally underlying the chamber generally comprises pressurizing the chamber to a first compression pressure to move blood in the limb from the region generally underlying the chamber. After pressurizing said at least one chamber to the first compression pressure, pressure in the chamber is reduced to a refill pressure to allow blood to reenter the region of the limb generally underlying the chamber. Pressure in the chamber is then sensed to determine a first venous refill time corresponding to an elapsed amount of time for venous blood flow in the limb to return to a steady state. The first three steps are repeated a second and other times using second and other compression pressures that are different from the first compression pressure and from each other. Second and other venous refill times are then determined. A customized compression pressure is determined by locating the compression pressure at which blood flow out of the region generally underlying the chamber is maximized by finding compression pressure at a maximum venous refill time. Compression therapy is applied to the limb with the sleeve including repeatedly pressurizing the chamber to the customized compression pressure and reducing pressure in the chamber.

In another aspect, a method for augmenting blood flow in a limb that is wrapped with a sleeve having at least one chamber capable of being pressurized for applying compression to the limb in a region generally underlying the chamber generally comprises pressurizing said at least one chamber to a first compression pressure to move blood in the limb from the region generally underlying the chamber. After pressurizing the chamber to the first compression pressure, pressure in the chamber is reduced to a refill pressure to allow blood to reenter the region of the limb generally underlying the chamber. By sensing pressure in the chamber, a first venous refill time corresponding to an elapsed amount of time for venous blood flow in the limb to return to a steady state after reducing said first compression pressure is determined. The first three steps are repeated at least one additional time to collect a set of first venous refill times. An average first venous refill time is calculated from the collected set of first venous refill times. The chamber is pressurized to a second and other compression pressures, said second and other compression pressures being different than said first compression pressure. After pressurizing the chamber to the second and other compression pressures, pressure in the chamber is reduced to a refill pressure to allow blood to reenter the region of the limb generally underlying the chamber. By sensing the pressure in the chamber, a second and other refill times corresponding to an elapsed amount of time for venous blood flow in the limb to return to a steady state after reducing said second and other compression pressure is determined. The steps directed to the second and other compression pressures are repeated at least one time to collect a set of second venous refill times and one or more sets of other venous refill times. An average second venous refill time is calculated from the collected set of second venous refill times. One or more average other venous refill times are calculated from said one or more sets of other venous refill times. A customized compression pressure is determined by locating the compression pressure at which blood flow out of the region generally underlying the chamber is maximized by finding compression pressure at a maximum venous refill time. Compression therapy is applied to the limb with the sleeve including repeatedly pressurizing said at least one pressurizable chamber to the calculated preferred pressure and reducing pressure in said at least one pressurizable chamber to allow venous refill.

In yet another aspect, a compression device generally comprises a sleeve adapted for wrapping around a limb of a person. The sleeve comprises at least one inflatable bladder for applying pressure to the limb and a compression control unit. The control unit includes a source of pressurized air and a valve in fluid communication with and downstream of the source of pressurized air to allow selected fluid connection between the source of pressurized air and the at least one inflatable bladder, and selected fluid communication between the at least one inflatable bladder and atmosphere. A pressure sensor is disposed for use in determining the fluid pressure in the inflatable bladder. The control unit further comprises a controller in electrical communication with the source of pressurized air, the valve, and the pressure sensor. The controller comprises a processor configured to execute computer-executable instructions for pressurizing the inflatable bladder to a first compression pressure to move blood in a region of the limb generally underlying the inflatable bladder when the sleeve is wrapped around the limb. After pressurizing said at least one chamber to the first compression pressure, pressure in said at least one inflatable bladder is reduced to a refill pressure to allow blood to reenter the region of the limb generally underlying the inflatable bladder. By sensing pressure in the inflatable bladder, a first venous refill time corresponding to an elapsed amount of time for venous blood flow in the limb to return to a steady state after reducing said first compression pressure is determined. The inflatable bladder is then pressurized to a second and other compression pressures, the second and other compression pressures being different than the first compression pressure. After pressurizing said at least one chamber to the second and other compression pressures, pressure in the inflatable bladder is reduced to a refill pressure to allow blood to reenter the limb region generally underlying the inflatable bladder. By sensing pressure in the inflatable bladder, second and other venous refill times corresponding to elapsed amounts of time for venous blood flow in the limb to return to a steady state after reducing said second and other compression pressures are determined. A customized compression pressure is determined by locating the compression pressure at which blood flow out of the region generally underlying the chamber is maximized by finding compression pressure at a maximum venous refill time. Compression therapy is applied to the limb with the sleeve including repeatedly pressurizing the inflatable bladder to the customized compression pressure and reducing pressure in said at least one pressurizable chamber to allow venous refill.

In still another aspect, a method for augmenting blood flow in a limb that is wrapped with a sleeve having at least one chamber capable of being pressurized for applying compression to the limb in a region generally underlying the chamber generally comprises pressurizing the chamber to a compression pressure to move blood in the limb from the region generally underlying the chamber. After pressurizing said at least one chamber to the first compression pressure, pressure in the chamber is reduced to a refill pressure to allow blood to reenter the region of the limb generally underlying the chamber. By sensing pressure in the chamber a venous refill time corresponding to an elapsed amount of time for venous blood flow in the limb to return to a steady state is determined. Memory stores the venous refill time. The first four steps are repeated a second and other times whereby a set of venous refill times are stored in the memory. The stored venous refill times are averaged and a time between reducing the compression pressure to the refill pressure and the next cycle of pressurizing the chamber based on the averaged venous refill time is adjusted.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
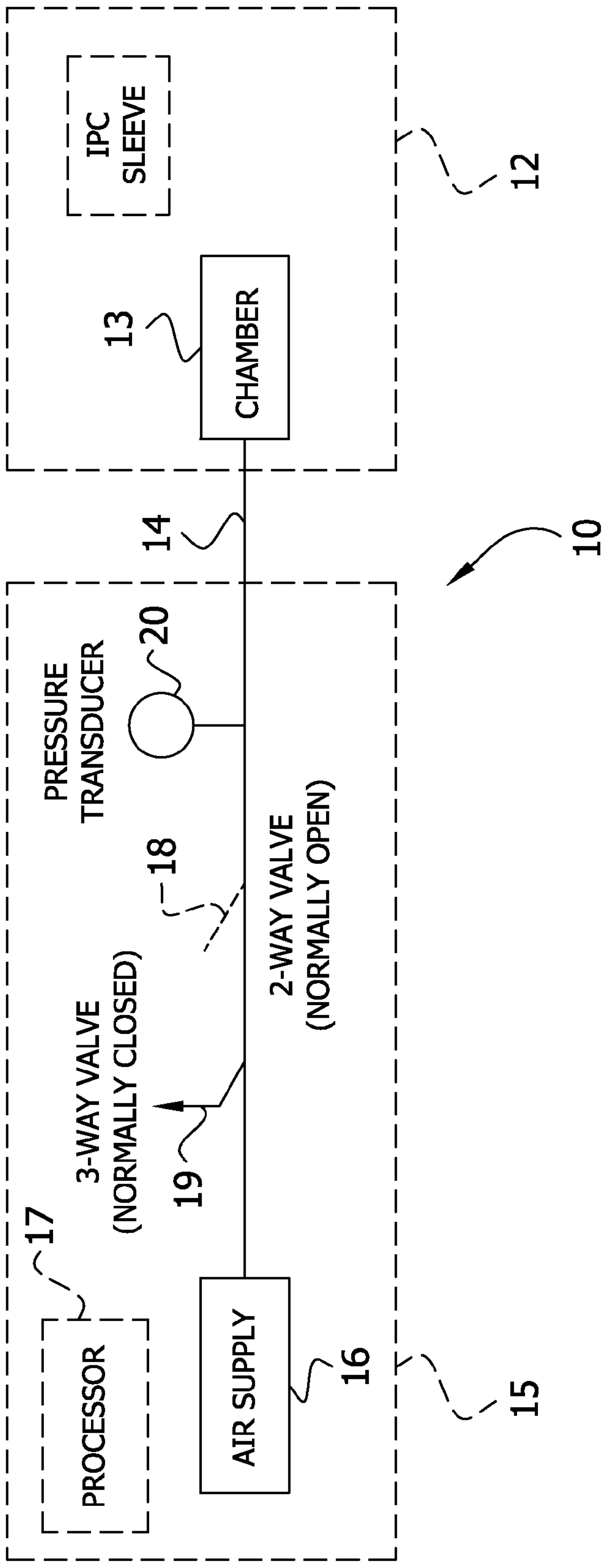
FIG. 1 is a pneumatic circuit implemented with a single-chambered sleeve of the present invention.

With reference to the figures, FIG. 1 in particular illustrates a pneumatic circuit in association with an intermittent pneumatic compression (IPC) device 10 to determine venous refill time according to the present invention. In the IPC device 10, a compression sleeve 12 having a single chamber 13 is connected, for example, via tubing 14, to a controller 15 having a processor 17 operatively connected to an air supply 16 (e.g., a compressor) which provides compressed air to the chamber of the sleeve. A two-way normally open valve 18 and a three-way normally closed valve 19 are provided between the sleeve 12 and the air supply 16. A pressure transducer 20 downstream of the valve 18 monitors the pressure in the chamber. The sleeve 12 can have two or more chambers without departing from the scope of the invention. For example, the sleeve 12 shown in FIG. 6 has three chambers 13.

Figure 6:
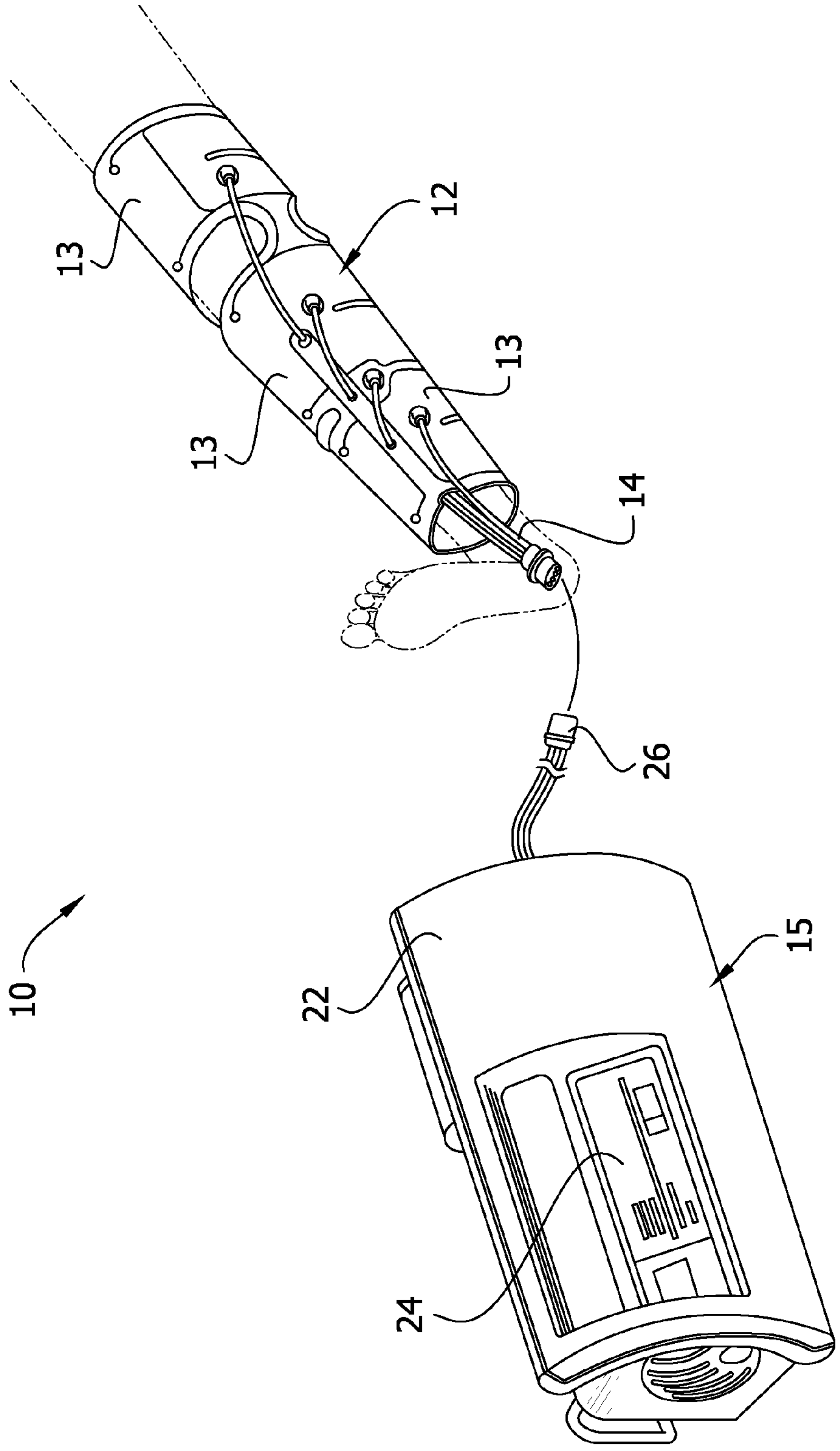
FIG. 6 is a perspective of a controller and compression sleeve of the present invention.

The sleeve 12 is configured to be wrapped around a patient's extremity (e.g., leg) (FIG. 6). To provide a compressive pulse to the leg, the valve 19 is opened and the air supply 16 is activated to provide compressed air to the chamber 13 until the pressure in the chamber reaches a suitable value for operation in a compression cycle, as is known in the art. Upon completion of the pressurization, the air supply 16 is deactivated and the chamber 13 is allowed to depressurize by, for example, venting back through the tubing to the controller. Air may be vented to the atmosphere through the three-way valve 19.

Figure 2:
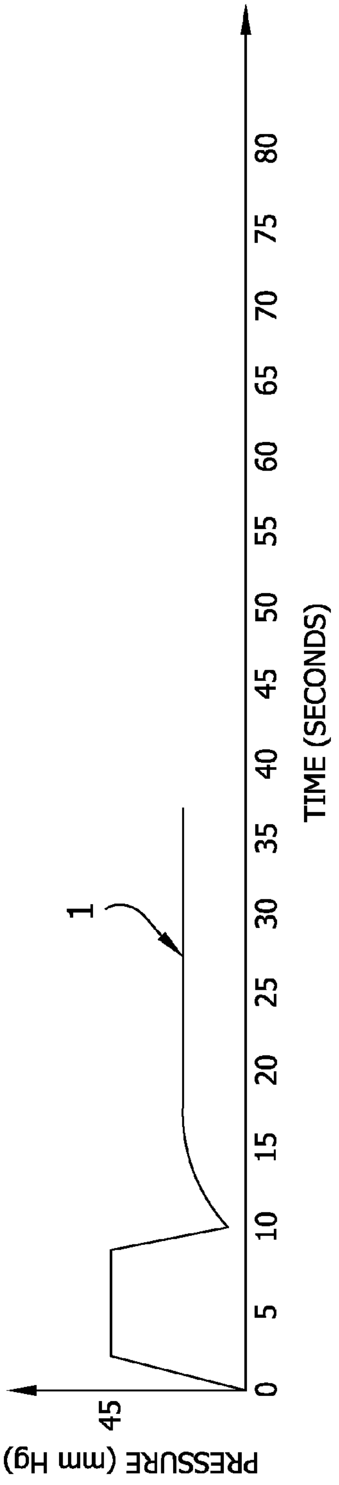
FIG. 2 PRIOR ART
FIG. 2 is a graph illustrating a prior art pressure profile during a procedure to determine venous refill time.
Figure 3:
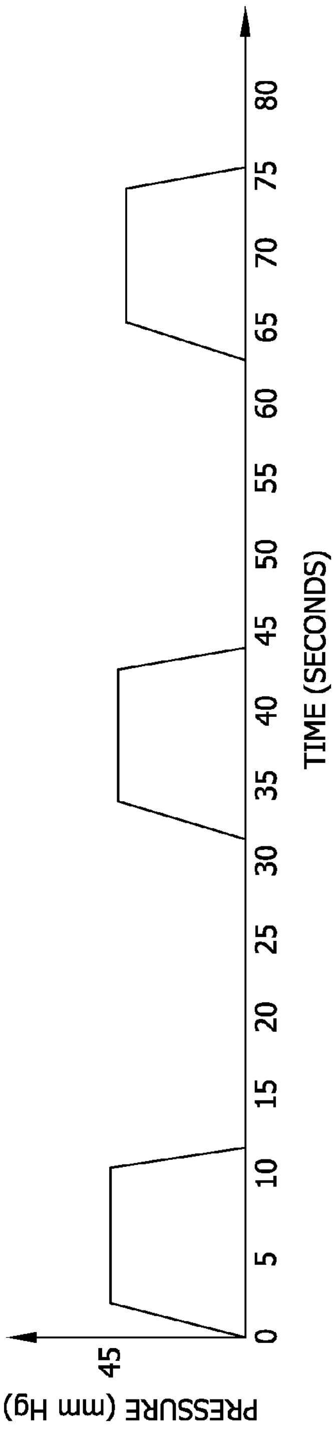
FIG. 3 PRIOR ART
FIG. 3 is a graph illustrating a prior art compression cycle after determining venous refill time.
Figure 4A:
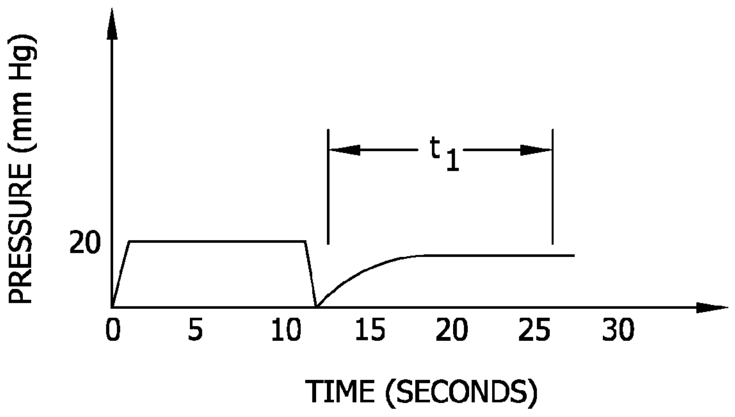
FIGS. 4A-4E are graphs illustrating a pressure profile during a procedure to determine venous refill time according to the present invention.
Figure 4B:
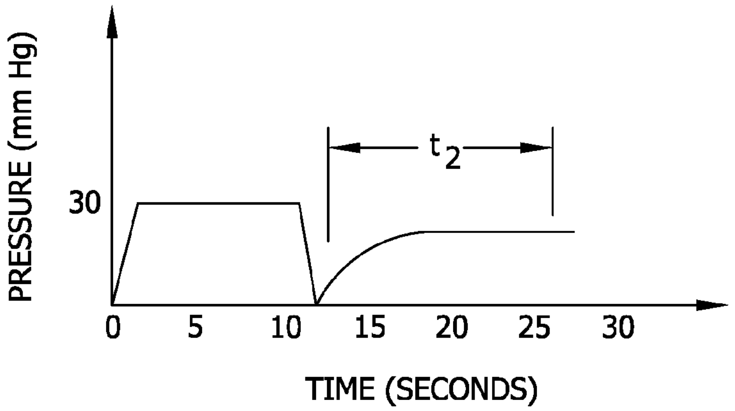
Figure 4C:
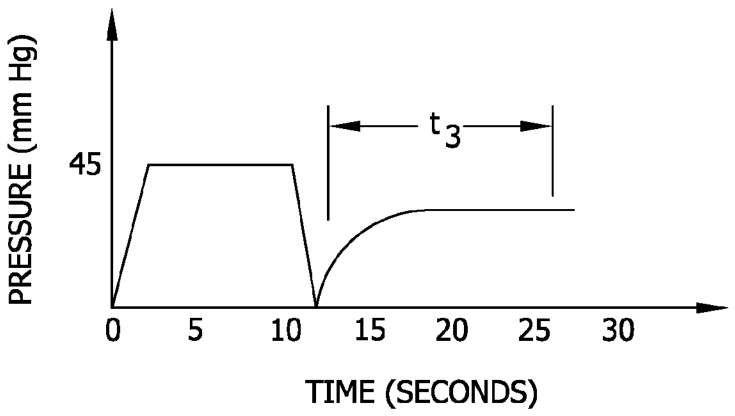
Figure 4D:
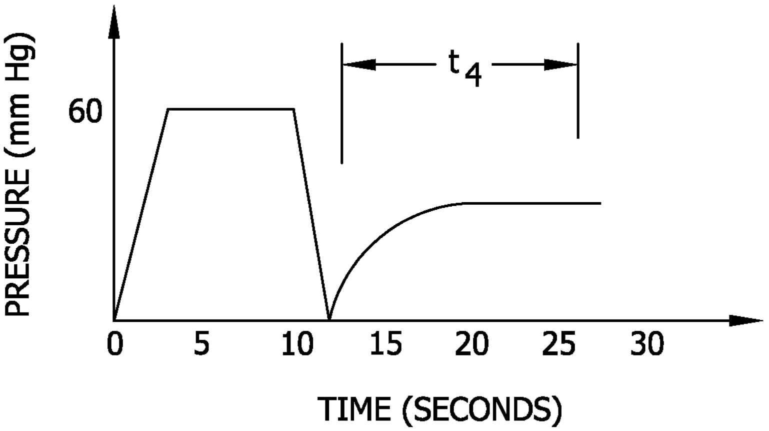
Figure 4E:
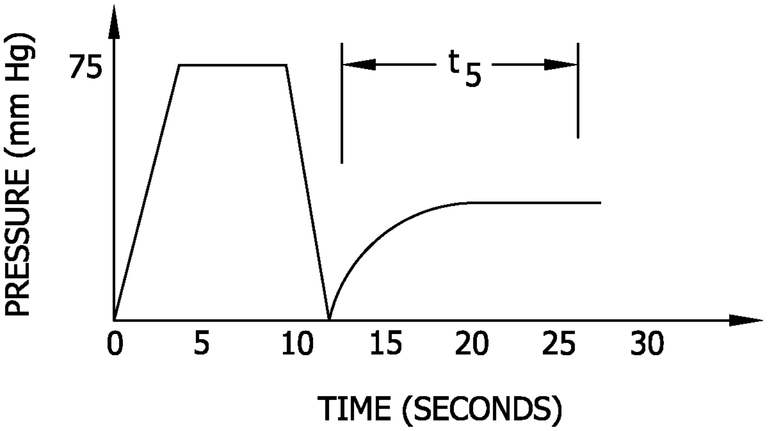

In prior art designs, when it is desired to determine the venous refill time for the patient, the chamber is permitted to depressurize until the pressure in that chamber reaches a lower value, typically 10 mm Hg (after approximately 2.5 seconds of depressurization). Alternatively, the chamber could be permitted to depressurize for a predetermined period of time. The two-way valve 18 is then closed to prevent further depressurization of the chamber. Alternatively, the chamber could be allowed to depressurize fully and could then be repressurized only until the pressure reaches the predetermined value, for example, 10 mm Hg. The pressure in the chamber is then sensed by the pressure transducer 20 for a time sufficient to allow the venous system in the leg to refill. The pressure rises as the leg gets larger, filling with blood. The pressure plateaus when the leg has refilled and returned to a steady state, indicated by the solid curve 1 in FIG. 2. The time between the start of depressurizing the pressurizable chamber and when this plateau occurs is determined to be the venous refill time and is taken by the controller 15 as the basis for the depressurization time for subsequent cycles. Based on this venous refill procedure, a compression cycle is performed at about 45 mm Hg with a depressurization time of about 20 seconds (FIG. 3).

Referring to FIGS. 4A-4E, in the present invention, the processor 17 is configured to execute computer-executable instruction to pressurize the chamber 13 to determine a customized venous refill time for the chamber. The computer-executable instructions for determining the venous refill time comprise pressurizing the chamber 13 to a first compression pressure (e.g., 20 mm Hg) to move the blood in the leg from a region (e.g., calf) underlying the chamber. After pressurizing the chamber 13 to the first compression pressure, the pressure in the chamber is reduced to a refill pressure (e.g., 10 mm Hg) to allow the blood to reenter the region of the limb underlying the chamber. The pressure in the chamber 13 is then sensed by the pressure transducer 20 until it is determined that blood flow has been completely restored to the region of the limb underlying the chamber. The time elapsed to restore blood flow is characterized as a first venous refill time $t_1$ and is stored by the controller 15. The chamber 13 is then pressurized to a second compression pressure (e.g., 30 mm Hg) and the same process is performed as was performed for the first compression pressure, resulting in a second venous refill time $t_2$. The chamber 13 can then be pressurized to even more compression pressures (e.g., 45, 60 and 75 mm Hg) and the process performed for the first and second compression pressures can be repeated for each pressure level to produce venous refill times $t_3$, $t_4$, $t_5$, $t_n$ for each additional pressure level. It is understood that pressure amounts other than those described above and shown in FIGS. 4A-4E can be used in the venous refill process without departing from the scope of the invention. Additionally, the venous refill process at each pressure level can be performed multiple times to produce multiple venous refill times for each pressure level.

Figure 5:
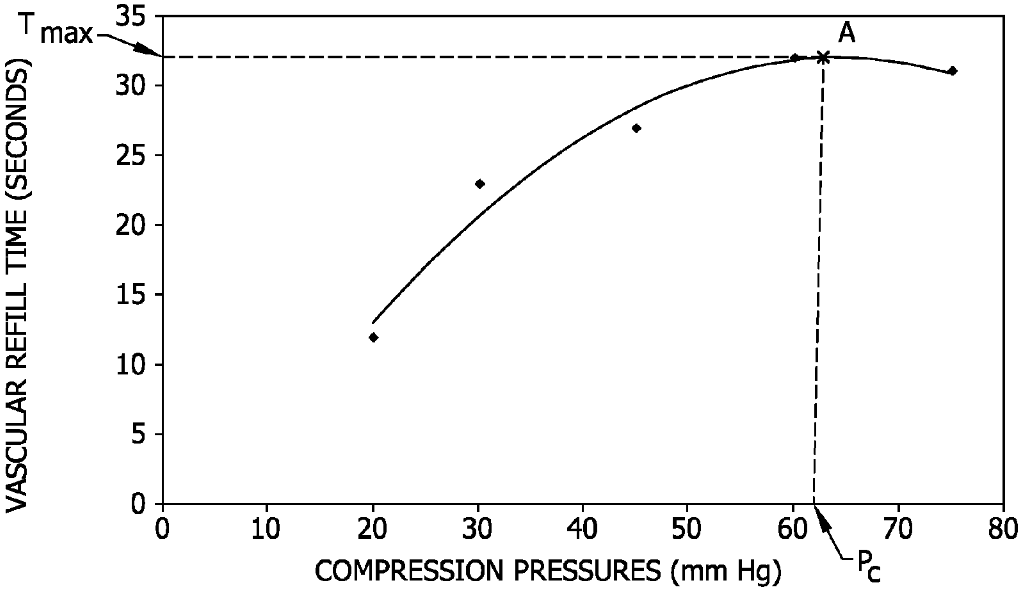
FIG. 5 is a graph illustrating a customized venous refill determination based on the pressure profiles in FIGS. 4A-4E.

Using the determined venous refill times $t_1$-$t_n$, the processor 17 determines a customized compression pressure by plotting the venous refill times for each selected pressure level on a graph as shown in FIG. 5 and fitting a best fit line to the plot using standard linear regression analysis. The apex A of the best fit line corresponds to a customized compression pressure $P_c$ for producing a maximum venous refill time $T_{max}$. The determined compression level $P_c$ and refill time $T_{max}$ are then incorporated into the compression therapy of the limb wherein the chamber 13 in the sleeve 12 is repeatedly pressurized to the customized compression pressure $P_c$, maintained at the customized compression pressure for a period of time and subsequently reduced to the refill pressure for the determined maximum refill time $T_{max}$ to facilitate blood circulation in the limb. In the instance where multiple venous refill times are recorded for each selected compression pressure level, the refill times are averaged by the processor 17 to produce an average value for the given pressure level. These average values are then plotted and a best fit line is fit to the plot of the average values and the customized compression pressure and maximum venous refill time are extrapolated from the plot in the same manner as described above. If the sleeve 13 includes multiple chambers (e.g., ankle, calf and thigh bladders as shown in FIG. 6), the controller 15 can be configured to operate the IPC device 10 to apply sequential compression therapy to the limb using the customized pressure and maximum refill time.

After applying compression therapy to the limb for a period of time the process for determining the customized compression pressure and maximum venous refill time can be repeated to determine new values. Additionally or alternatively, memory in the controller 15 can record the venous refill times sensed by the pressure transducer 20 during the compression therapy and average the recorded values to adjust the time between consecutive pressurizations of the chamber 13 based on the averaged refill times. These two processes ensure that the compression therapy being delivered to the limb adapts to the changing characteristics of the limb so that a customized compression therapy is delivered to the limb through the duration of the compression therapy.

Referring to FIG. 6, the controller 15 is located in a housing 22. A control or front panel 24 on the housing 22 includes controls and indicators for operation. An output connector 26 is disposed on the housing 22 and is adapted to receive the tubing 14 for connecting the controller 15 and air supply 16 to the sleeve 13. FIG. 6 shows an embodiment of the IPC device 10 wherein the sleeve 12 includes three chambers 13.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A compression device comprising:

a sleeve adapted for wrapping around a limb of a person, the sleeve comprising at least one inflatable bladder for applying pressure to the limb;

a compression control unit including:

a source of pressurized air;

a valve in fluid communication with and downstream of the source of pressurized air to allow selected fluid connection between the source of pressurized air and the at least one inflatable bladder, and selected fluid communication between the at least one inflatable bladder and atmosphere;

a pressure sensor disposed for use in determining the fluid pressure in the inflatable bladder; and a controller in electrical communication with the source of pressurized air, the valve, and the pressure sensor, the controller comprising computer-executable instructions and a processor configured to execute the computer-executable instructions, the computer-executable instructions comprising instructions for:

(a) pressurizing the at least one inflatable bladder to a first compression pressure to move blood in a region of the limb generally underlying the at least one inflatable bladder when the sleeve is wrapped around the limb;

(b) reducing pressure in said at least one inflatable bladder, after pressurizing said at least one inflatable bladder to the first compression pressure, to a refill pressure to allow blood to reenter the region of the limb generally underlying the at least one inflatable bladder;

(c) determining, by sensing pressure in the at least one inflatable bladder, a first venous refill time corresponding to an elapsed amount of time for venous blood flow in the limb to return to a steady state after reducing said first compression pressure;

(d) pressurizing the at least one inflatable bladder to a second and other compression pressures, the second and other compression pressures being different than the first compression pressure;

(e) reducing pressure in the at least one inflatable bladder, after pressurizing said at least one inflatable bladder to the second and other compression pressures, to a refill pressure to allow blood to reenter the limb region generally underlying the at least one inflatable bladder;

(f) determining, by sensing pressure in the at least one inflatable bladder, second and other venous refill times corresponding to elapsed amounts of time for venous blood flow in the limb to return to a steady state after reducing said second and other compression pressures;

(g) determining a customized compression pressure by locating the compression pressure at which blood flow out of the region generally underlying the at least one inflatable bladder is maximized by finding the compression pressure at a maximum venous refill time, using said first, second, and other compression pressures and said first, second, and other venous refill times;

(h) applying compression therapy to the limb with the sleeve including repeatedly pressurizing the at least one inflatable bladder to the customized compression pressure and reducing pressure in said at least one inflatable bladder to allow venous refill.

2. A compression device as set forth in claim 1 wherein the sleeve includes a plurality of inflatable bladders, the controller includes computer executable instructions to operate the compression control unit to apply sequential compression therapy to the limb with the sleeve using the customized pressure.

3. A compression device as set forth in claim 1 wherein the controller includes computer executable instructions to determine a new customized pressure at a predetermined time.

4. A compression device as set forth in claim 1 wherein the controller includes computer executable instructions to repeat steps (a)-(c) multiple times before executing step (d), to generate multiple first venous refill times at the first compression pressure, the controller further including computer-executable instructions for averaging the first venous refill times, and to use the average first venous refill time in step (g).

5. A compression device as set forth in claim 1 wherein the controller includes a memory area for storing venous refill times acquired during step (h) and computer-executable instructions for averaging the acquired venous refill times and adjusting a time between consecutive inflations of the at least one inflatable bladder to correspond to the averaged venous refill time.

6. A compression device as set forth in claim 1 wherein the computer executable instructions for determining the customized compression pressure further comprise fitting a curve to a plot of the first, second, and other compression pressures against the first, second, and other venous refill times.

7. A compression device as set forth in claim 6 wherein the computer executable instructions for determining customized compression pressure further comprise finding the compression pressure at the apex of the curve corresponding to the maximum venous refill time.

* * * * *

UNITED STATES PATENT AND TRADEMARK OFFICE

CERTIFICATE OF CORRECTION

PATENT NO. : 8,506,507 B2
APPLICATION NO. : 12/720122
DATED : August 13, 2013
INVENTOR(S) : Malcolm G. Bock and Kristin L. Watson It is certified that error appears in the above-identified patent and that said Letters Patent is hereby corrected as shown below:

On the Title Page, Item (12) “Bock” should read -- Bock et al. --

On the Title Page, Item (75), Inventor:

“Malcolm G. Bock”

Should read

-- Malcolm G. Bock and Kristin L. Watson --

Signed and Sealed this
Twenty-second Day of October, 2013

Teresa Stanek Rea
*Deputy Director of the United States Patent and Trademark Office*